United States Patent [19]

Slocum et al.

[11] Patent Number: 4,959,176

[45] Date of Patent: Sep. 25, 1990

[54] HIGH RESOLUTION NON CORROSIVE AMINO ACID ANALYSIS BUFFER SOLUTIONS

[75] Inventors: Robert H. Slocum, Portola Valley; Patrick L. Y. Lee, Belmont; Vivian Arrizon-Lopez, San Jose, all of Calif.

[73] Assignee: Beckman Instruments, Inc., Fullerton, Calif.

[21] Appl. No.: 187,702

[22] Filed: Apr. 29, 1988

[51] Int. Cl.$^5$ .................. G01N 30/96; C23F 11/04
[52] U.S. Cl. .................. 252/389.53; 252/389.62; 252/396; 136/8
[58] Field of Search ............ 252/1, 389.62, 396, 252/389.53; 436/8

[56] References Cited

U.S. PATENT DOCUMENTS

| | | | |
|---|---|---|---|
| 4,304,707 | 12/1981 | Kuehn | 252/396 |
| 4,401,624 | 8/1983 | Atwater | 252/389.62 X |
| 4,482,759 | 11/1984 | Schawrze et al. | 252/396 X |
| 4,728,452 | 4/1988 | Hansen | 252/389.62 X |
| 4,743,393 | 5/1988 | Hirozawa | 252/389.2 X |

OTHER PUBLICATIONS

Pierce Chemical Company's Sales Literature; "Buffelute TM High Performance Buffers for Amino Acid Analysis".

Benson, James R.; "Amino Acid Analysis Using Halide-Free Elements"; 41, Federation Proceeding, 4, (Mar. 5, 1982).

*Primary Examiner*—John S. Maples
*Assistant Examiner*—Valerie D. Fee
*Attorney, Agent, or Firm*—William H. May; Paul R. Harder; Wen Liu

[57] ABSTRACT

Aqueous buffer solutions for use in an ion exchange amino acid analysis system compounded so that it is non-corrosive to the stainless steel components of such a system while achieving high resolution and short analysis times in separation of the various amino acids in a sample mixture. The aqueous buffer preferably comprising a mixture of salts free of halogen ions but containing nitrate ions which tend to passivate stainless steel preventing corrosion.

9 Claims, No Drawings

HIGH RESOLUTION NON CORROSIVE AMINO ACID ANALYSIS BUFFER SOLUTIONS

BACKGROUND OF THE INVENTION

The present invention is directed to the formulation of aqueous buffer solutions for use with ion exchange amino acids analysis systems and, more particularly for use with systems incorporating stainless steel components. In the instance of amino acid analysis systems, designed for achieving separations by ion exchange chromatography, it is usual to utilize special and quite expensive stainless materials such as Carpenter 20 and Inconel in order to withstand the corrosive composition of the conventional buffer solutions. Dedicated ion exchange amino acids analysis instruments are usually very sophisticated, expensive and, therefore not widely available. HPLC (High Performance Liquid Chromatography) instruments, on the other hand, are relatively inexpensive, widely available and are also used for amino acid analysis by so called reverse phase methods. In general the reverse phase methods are not as satisfactory as ion exchange methods; which are used to establish the standard for all other methods. Because components of the HPLC systems such as pumps, sample injectors, motorized valves, chromatography columns and so on are similar to those in an ion exchange chromatography instrument, there have been many attempts to incorporate an ion exchange column in an HPLC instrument so that it could be used to perform the classic Moore & Stein amino acid analysis. It was quickly discovered that the conventional buffers for ion exchange chromatography rapidly attacked the stainless steel components of HPLC systems not only shortening the life of the components but also, because of the resulting metal ions, rapidly spoiling the performance of the ion exchange resins. A number of attempts to overcome this problem by eliminating from the buffer solutions constituents, such as chloride ions, known to be corrosive to stainless steel have been described in the literature and, in one instance is commercially available. Unfortunately, while corrosion was eliminated the overall chromatographic performance of these buffers is not equal to the chloride containing buffers used in the dedicated ion exchange amino acid analysis systems and, therefore, the users need for performance equivalent to that of a dedicated ion exchange amino acid analyser is not met.

SUMMARY OF THE INVENTION

It is, therefore, an object of the present invention to provide buffer solutions for ion exchange amino acid analysis systems that are non-corrosive to the stainless steels used in conventional HPLC chromatography systems.

It is a further object of the present invention to provide buffer solutions that will achieve separations of amino acids by ion exchange chromatography that are equal to that achieved with conventional corrosive buffer solutions in dedicated ion exchange chromatography instruments when utilized with HPLC systems incorporating ordinary stainless steel components.

It is yet another object of the present invention to provide buffer solutions that will provide uncompromised analytical determination and separation of both simple and complex amino acid mixtures.

Other objects and advantages will become evident as the detailed description of the present invention proceeds.

DETAILED DESCRIPTION OF THE INVENTION

The above and other objects and advantages of the invention are achieved by one or more buffer solutions consisting essentially of distilled or deionized water containing:

(a) sodium citrate from 0.5 to 5% by weight
(b) sodium nitrate from 0 to 6% by weight
(c) concentrated nitric acid from 0.01 to 4% by volume
(d) benzoic acid from 0 to 0.1% by weight
(e) ethylmercurithiosalicylic acid from 0 to 0.003% by weight said buffer solutions to be compounded so that the sodium ion concentration is in the range of 0.12N to 1.2N. Depending on the application the buffer solution will be compounded to have pH values in the range of 1.0 to 6.9.

It will be understood by those skilled in the art that useful ion exchange buffer solutions can be prepared with substitution of lithium, potassium, rubidium or cesium; totally, or in part, for sodium (with due adjustment for the different molecular weights). Similarly, though less well known, it is possible to substitute other tribasic acid salts, in whole or in part for the citrate salt. Both the benzoic acid and the ethylmercurithiosalicylic acid serve as mold growth inhibitors for which there are many well known substitutes such as phenol, toluene and octanoic acid.

In many instances involving the separation of complex mixtures of amino acids by ion exchange chromatography it is usual to use two or more buffer solutions with differing pH values, switching from one to another, in the course of a single analytical run. One preferred set of such buffer solutions, formulated in accordance with the above disclosed guidelines, is described in Table 1 below:

TABLE 1

| Buffer | Chloride Free Hydrolysate Buffers | | |
|---|---|---|---|
|  | I | II | III |
| pH | 3.28 | 4.24 | 6.39 |
| Sodium Concentration(N) | 0.20 | 0.20 | 0.75 |
| Sodium Citrate 2H$_2$O (gms) | 19.61 | 19.61 | 19.61 |
| Sodium Nitrate (gms) | 0 | 0 | 46.80 |
| Concentrated Nitric Acid (ml) | 16.0 | 12.0 | 0.05 |
| Benzoic Acid (gms) | 0.25 | 0.25 | 0 |
| Ethylmercurithiosalicylic Acid (gms) | 0 | 0 | 0.01 |
| Water to make final volume (ml) | 1000 | 1000 | 1000 |

Separation of complex mixtures made with these chloride-free buffers are quite comparable to those using traditional chloride-containing buffers. Resolution of closely eluting doublets (valley-to-peak ratios) are on the order of 75% These doublets (typically Threonine/Serine) generally show resolution of less than 50% with prior art chloride-free buffers. For comparison the quantities of amino acids separated from identical samples with the chloride containing and the chloride free buffer systems are shown in Table 2 below:

TABLE 2

Valley to peak Ratios of Chloride and Non-Chloride Buffers
% Resolved

| Peak Number | Amino Acid | Cl- Buffer | non-Cl- Buffer |
|---|---|---|---|
| 1 | CYS $O_2$ | 100 | 100 |
| 2 | MET O | 100 | 98 |
| 3 | ASP | 87.4 | 88.2 |
| 4 | MET $O_2$ | 89.2 | 88.6 |
| 5 | THR | 82.7 | 71.9 |
| 6 | SER | 100 | 100 |
| 7 | H SER | 100 | 97.2 |
| 8 | GLU | 100 | 100 |
| 9 | PRO | 100 | 100 |
| 10 | GLY | 98.2 | 100 |
| 11 | ALA | 100 | 100 |
| 12 | CYS | 98.1 | 99.5 |
| 13 | VAL | 100 | 100 |
| 14 | MET | 100 | 100 |
| 15 | ILE | 90.6 | 94 |
| 16 | LEU | 94.7 | 86.6 |
| 17 | NLE | 93.6 | 100 |
| 18 | TYR | 100 | 95.5 |
| 19 | PHE | 100 | 100 |
| 20 | HIS | 100 | 100 |
| 21 | H SER L | 100 | 100 |
| 22 | OH LYS | 100 | 100 |
| 23 | LYS | 100 | 100 |
| 24 | TRP | 100 | 100 |
| 25 | $NH_3$ | 100 | 100 |
| 26 | ARG | 100 | 100 |

Over a six months period over 700 sample analyses were performed with these buffers on an automatic amino acid analyser in which the ion exchange resin supports were stainless steel sintered disks. There was no significant reduction in column resolution and no indication that the ion exchange resin was degrading over the course of this experiment. With traditional chloride containing buffers the disks would have dissolved and, well before mechanical failure, metallic ions would have ruined the performance of the ion-exchange resin.

A series of separations were run, with the same set of buffers, on a sample mixture of 17 amino acids and $NH_3$ to determine retention time and concentration reproducibility. Retention time coefficients of variation range from 0.05 to 0.43% with a mean value of 0.23%. Concentration coefficients of variation, Table 3, range from 0.44 to 1.70% with a mean value of 0.83%.

TABLE 3

CONCENTRATION REPRODUCIBILITY
(nanomoles per 50 microliters)

| NAME | 1 | 2 | 3 | 4 | 5 | 6 | MEAN | RSD % |
|---|---|---|---|---|---|---|---|---|
| ASP | 4.86 | 5.05 | 5.00 | 4.98 | 5.00 | 4.97 | 4.979 | 1.26 |
| THR | 5.06 | 5.08 | 5.00 | 4.97 | 5.01 | 4.96 | 5.013 | 1.01 |
| SER | 4.79 | 5.01 | 5.01 | 5.00 | 4.98 | 5.00 | 4.966 | 1.71 |
| GLU | 4.96 | 5.06 | 5.00 | 4.98 | 4.99 | 4.97 | 4.993 | 0.67 |
| PRO | 5.05 | 5.06 | 5.10 | 4.99 | 5.01 | 4.98 | 5.031 | 0.96 |
| GLY | 5.01 | 5.06 | 5.02 | 5.00 | 5.00 | 4.99 | 5.012 | 0.54 |
| ALA | 4.97 | 5.06 | 5.02 | 4.98 | 5.00 | 4.97 | 4.999 | 0.67 |
| CYS* | 2.50 | 2.54 | 2.50 | 2.49 | 2.50 | 2.49 | 2.505 | 0.63 |
| VAL | 5.01 | 5.11 | 5.05 | 5.01 | 5.01 | 5.01 | 5.033 | 0.78 |
| MET | 5.04 | 5.07 | 5.01 | 4.99 | 5.01 | 5.00 | 5.019 | 0.57 |
| ILE | 5.03 | 5.07 | 5.02 | 4.98 | 5.01 | 5.00 | 5.018 | 0.58 |
| LEU | 5.02 | 5.06 | 5.01 | 4.98 | 5.00 | 5.00 | 5.009 | 0.56 |
| TYR | 5.03 | 5.06 | 5.02 | 4.99 | 5.01 | 5.00 | 5.018 | 0.51 |
| PHE | 5.01 | 5.05 | 5.00 | 4.98 | 5.00 | 4.99 | 5.006 | 0.44 |
| HIS | 5.02 | 5.07 | 5.02 | 5.01 | 5.01 | 5.01 | 5.022 | 0.46 |
| LYS | 5.04 | 5.05 | 5.01 | 4.99 | 5.01 | 5.01 | 5.019 | 0.45 |
| $NH_3$ | 5.13 | 4.99 | 5.06 | 4.96 | 5.11 | 4.77 | 5.003 | 2.67 |
| ARG | 4.99 | 5.03 | 5.05 | 5.04 | 5.02 | 5.03 | 5.026 | 0.44 |

*CYS present at 2.5 nanomoles per 50 microliters

These results, show that the separation performance of these buffer solutions is in every way equal to that of the traditional chloride containing buffer solutions.

When separating free amino acids in physiological fluids by ion exchange chromatography key separations are achieved only with lithium rather than sodium type buffer solutions. A preferred set of such lithium type buffer solutions is described in Table 4 below:

TABLE 4

Chloride Free Physiological Fluid Buffers

| Buffer | I | II | III | IV |
|---|---|---|---|---|
| pH | 2.83 | 3.33 | 3.57 | 3.98 |
| Lithium Concentration(N) | .20 | 0.30 | 0.60 | 0.95 |
| Citric Acid.$H_2O$ (gms) | 9.61 | 13.50 | 13.50 | 13.50 |
| Lithium Hydroxide.$H_2O$ (gms) | 8.40 | 8.40 | 8.40 | 8.40 |
| Lithium Nitrate (gms) | 0 | 6.89 | 27.58 | 20.04 |
| Conc. Nitric Acid (ml) | 8.40 | 12.00 | 6.00 | 15.00 |
| Benzoic Acid (gms) | 0.25 | 0.25 | 0.25 | 0.25 |
| Water to make final vol.(ml) | 1000 | 1000 | 1000 | 1000 |

The separations and peak resolutions achieved with this set of buffer solutions is equally satisfactory with that obtained on physiological fluids using conventional lithium type chloride containing buffers.

It is understood that the examples and embodiments described herein are for illustrative purposes only and various modifications or changes in light thereof will be suggested to persons skilled in the art and are to be included within the spirit and purview of this application and the scope of the appended claims.

What is claimed is:

1. An aqueous buffer solution for separating the components of a mixed amino acid sample by the ion exchange method which is essentially halogen free and comprising alkali metal salts of tribasic organic acids, alkali metal nitrates, nitric acid and a mold inhibiting agent.

2. A buffer solution as in claim 1 in which the alkali metal is selected from the group consisting of sodium, lithium and potassium.

3. A buffer solution as in claim 2 in which the tribasic organic acid salt is citrate.

4. A buffer solution as in claim 3 in which the alkali metal is sodium and sodium citrate concentration is between 0.5 and 5% by weight, sodium nitrate concentration is up to 6% by weight, the nitric acid is of concentration between 0.01 and 4% by volume, and the mold inhibiting agent comprises benzoic acid of concentration between 0 and 0.1% by weight and ethylmercurithiosalicylic acid from 0 to 0.003% by weight.

5. A buffer solution as in claim 4 in which the pH is 3.28, the sodium citrate concentration is 1.721% by weight, nitric acid concentration is 1.6% by volume and benzoic acid concentration is 0.025% by weight.

6. A buffer solution as in claim 4 in which the pH is 6.39, the sodium citrate concentration is 1.721% by weight, the sodium nitrate concentration is 4.68% by weight, the nitric acid concentration is 0.005% by volume and the Ethylmercurisalicyclic acid concentration is 0.001% by weight.

7. A buffer solution as in claim 3 in which the alkali metal is lithium and the pH is 3.98, lithium nitrate concentration is 2% by weight, the nitric acid concentration is 1.5% by volume and the mold inhibiting agent comprises benzoic acid of concentration 0.025% by weight.

8. An aqueous buffer solution non-corrosive to stainless steel consisting essentially of sodium citrate, sodium nitrate, nitric acid, a mold inhibiting agent and water.

9. An aqueous buffer solution non-corrosive to stainless steel consisting essentially of citric acid, lithium hydroxide, lithium nitrate, nitric acid, a mold inhibiting agent and water.

* * * * *